US 8,722,905 B2

(12) United States Patent
Wu et al.

(10) Patent No.: US 8,722,905 B2
(45) Date of Patent: May 13, 2014

(54) DYES AND PHOTOELECTRIC CONVERSION DEVICES CONTAINING THE SAME

(75) Inventors: Yao-Shan Wu, Kaohsiung (TW); Yung-Liang Tung, Hsinchu County (TW); Jen-An Chen, Miaoli County (TW); Chun-Guey Wu, Hualien County (TW); Jheng-Ying Li, Taoyuan County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/566,697

(22) Filed: Aug. 3, 2012

(65) Prior Publication Data

US 2013/0261314 A1    Oct. 3, 2013

(30) Foreign Application Priority Data

Mar. 28, 2012    (TW) .............................. 101110730 A (51) Int. Cl.
C07D 209/84    (2006.01)

(52) U.S. Cl.
USPC ...................... 548/446; 548/371.4; 548/305.1; 546/200; 546/170; 544/333; 544/279; 544/257

(58) Field of Classification Search
None
See application file for complete search history.

(56) References Cited

U.S. PATENT DOCUMENTS

| | | | |
|---|---|---|---|
| 6,191,278 B1 | 2/2001 | Lee et al. |
| 6,372,907 B1 | 4/2002 | Lee et al. |
| 6,811,979 B2 | 11/2004 | Taing et al. |
| 7,429,651 B2 | 9/2008 | Taing et al. |
| 7,432,298 B2 | 10/2008 | Lam et al. |
| 7,491,830 B2 | 2/2009 | Lam et al. |
| 7,504,496 B2 | 3/2009 | Lee et al. |
| 7,687,236 B2 | 3/2010 | Taing et al. |
| 7,795,042 B2 | 9/2010 | Lee et al. |
| 8,003,096 B2 | 8/2011 | Carmeliet et al. |
| 2002/0102590 A1 | 8/2002 | Taing et al. |
| 2003/0031627 A1 | 2/2003 | Rajagopalan et al. |
| 2003/0055257 A1 | 3/2003 | Lee et al. |
| 2004/0151667 A1 | 8/2004 | Rajagopalan et al. |
| 2004/0225037 A1 | 11/2004 | Lam et al. |
| 2004/0242902 A1 | 12/2004 | Lam et al. |
| 2005/0153355 A1 | 7/2005 | Lee et al. |
| 2005/0250119 A1 | 11/2005 | Taing et al. |
| 2009/0016965 A1 | 1/2009 | Rajagopalan et al. |
| 2009/0072197 A1 | 3/2009 | Lam et al. |
| 2009/0092986 A1 | 4/2009 | Taing et al. |
| 2009/0172899 A1 | 7/2009 | Lam et al. |
| 2009/0305433 A1 | 12/2009 | Lee et al. |
| 2010/0035359 A1 | 2/2010 | Cormack et al. |
| 2010/0304381 A1 | 12/2010 | Taing et al. |
| 2011/0081688 A1 | 4/2011 | Lee et al. |
| 2011/0177006 A1 | 7/2011 | Rajagopalan et al. |
| 2011/0177007 A1 | 7/2011 | Rajagopalan et al. |
| 2011/0180791 A1 | 7/2011 | Pan et al. |
| 2011/0196231 A1 | 8/2011 | Rajagopalan et al. |
| 2011/0226994 A1 | 9/2011 | Lam et al. |
| 2011/0264026 A1 | 10/2011 | Rajagopalan |
| 2011/0288033 A1 | 11/2011 | Rajagopalan |

FOREIGN PATENT DOCUMENTS

| | | |
|---|---|---|
| JP | 2001076773 A | 3/2001 |
| JP | 2006063034 A | 3/2006 |
| JP | 2008177147 A | 7/2008 |
| JP | 2008311127 A | 12/2008 |
| JP | 2011060503 A | 3/2011 |
| TW | 211035 B | 8/1993 |
| TW | 575646 B | 2/2004 |
| TW | 586053 | 5/2004 |
| TW | 200614394 | 5/2006 |
| TW | 200617994 | 6/2006 |
| TW | 200623342 | 7/2006 |
| TW | 200702366 | 1/2007 |
| TW | 200745303 | 12/2007 |
| TW | 200921657 A | 5/2009 |
| TW | 200936506 | 9/2009 |
| TW | I314237 B | 9/2009 |
| TW | 200946599 A | 11/2009 |
| TW | I317256 B | 11/2009 |
| TW | 201019518 | 5/2010 |
| TW | I327251 B | 7/2010 |
| TW | 201029957 | 8/2010 |
| TW | 201123578 | 7/2011 |
| WO | WO-2009/053107 A1 | 4/2009 |
| WO | WO-2009/053108 A1 | 4/2009 |
| WO | WO-2010104117 A1 | 9/2010 |

OTHER PUBLICATIONS

Li et al. Journal of Chinese Chemical Society, vol. 59 (10), 1337-1344 (2012).*
Anthony Burke et al., A novel blue dye for near-IR "dye-sensitised" solar cell applications, The Royal Society of Chemistry, 2007, pp. 234-236.
Shigeyuki Yagi et al., The synthesis and optical properties of bis-squarylium dyes bearing arene and thiophene spacers, ScienceDirect—Dyes and Pigments 77, 2008, pp. 525-536, Elsevier.
Shyam S. Pandey et al., Substituent effect in direct ring functionalized squaraine dyes on near infra-red sensitization of nanocrystalline TiO2 for modulecular photovoltaics, Journal of Photochemistry and Photobiology A: Chemistry, 2010, pp. 269-275, vol. 214, Elsevier.
Chao Li, Molecular Design of Squaraine Dyes for Efficient Far-red and Near-IR Sensitization of Solar Cells, Chemistry Letters, 2005, pp. 554-555, vol. 34, No. 4.
Saji Alex et al., Dye Sensitization of nanocrystalline TiO2: enhanced efficiency of unsymmetrical versus symmetrical squaraine dyes, Journal of Photochemistry and Photobiology A: Chemistry, 2005, pp. 63-71, vol. 172, Elsevier.

* cited by examiner

*Primary Examiner* — Nyeemah A Grazier
(74) *Attorney, Agent, or Firm* — Muncy, Geissler, Olds & Lowe, P.C.

(57) ABSTRACT

Disclosed is a dye, having a chemical formula:

wherein each $R^1$ is independently selected from hydrogen, $-(C_xH_{2x+1})$, $-(C_yH_{2y})-S-(C_xH_{2x+1})$, or $-(C_yH_{2y})-N(C_xH_{2x+1})_2$; $Ar^1$ is wherein each $R^2$ is independently selected from $-(C_xH_{2x+1})$, $-(C_xH_{2x})-S-(C_xH_{2x+1})$, or $(C_xH_{2x})-N(C_xH_{2x+1})_2$; $Ar^2$ is wherein each $R^3$ is independently selected from hydrogen, $-(C_xH_{2x+1})$, $-(C_yH_{2y})-S-(C_xH_{2x+1})$, or $-(C_yH_{2y})-N(C_xH_{2x+1})_2$; X is sulfur, oxygen, selenium, or $N-R^4$, and $R^4$ is $-(C_xH_{2x+1})$; m is in integer of 1 to 4; x is an integer of 1 to 20; and y is an integer of 0 to 20. The dye can be applied to a photoelectric conversion device.

11 Claims, 2 Drawing Sheets

DYES AND PHOTOELECTRIC CONVERSION DEVICES CONTAINING THE SAME

CROSS REFERENCE TO RELATED APPLICATIONS

This application is based upon and claims the benefit of priority from the prior Taiwan Patent Application No. 101110730, filed on Mar. 28, 2012, the entire contents of which are incorporated herein by reference.

TECHNICAL FIELD

The disclosure relates to a dye, and in particular relates to a dye applied in an optoelectronic conversion device.

BACKGROUND

Several alternative renewable energies have been discovered to meet the energy saving requirements. Recently, Grätzel and O'Regan have disclosed a dye-sensitized solar cell (DSSC) for efficiently utilizing solar energy, thereby largely attracting industry attention. A general DSSC structure includes four parts: an anode/cathode to provide a flow path of current, a semiconductor $TiO_2$ to accept electrons, a dye layer, and an electrolyte to transport electron holes. Materials of the DSSC parts and interface structures between the DSSC parts may influence a device efficiency of the DSSC; however, a dye in the dye layer is most critical in the DSSC. As such, a dye molecule may reach the best efficiency of the DSSC is one of the topics in this field.

A dye with a complex with a ruthenium center (e.g. N3 dye, (cis-dithiocyanato-bis(4,4'-dicarboxy-2,2'-bipyridine) ruthenium) has the highest conversion efficiency among the conventional dyes. However, ruthenium costs expensive due to its low reserves. A novel dye is called-for to replace the best ruthenium dye N3. For example, organic dyes are candidates due to their high absorption coefficient, tunable structure, and easily obtainable properties; especially their high absorption coefficient thereof (the most critical property of photo sensitive dyes). As such, organic dyes have excellent development potential.

Although the organic dyes have many advantages as described above, there is no organic dye really utilized in a DSSC due to their low stability, low durability, and low conversion efficiency. Therefore, designing a novel organic dye having high absorption coefficient and high conversion efficiency is a topic in the field of optoelectronic conversion devices.

SUMMARY

One embodiment of the disclosure provides a dye, having a chemical formula:

wherein each $R^1$ is independently selected from hydrogen, —($C_xH_{2x+1}$), —($C_yH_{2y}$)—S—($C_xH_{2x+1}$), or —($C_yH_{2y}$)—N($C_xH_{2x+1}$)$_2$; $Ar^1$ is wherein each $R^2$ is independently selected from —($C_xH_{2x+1}$), —($C_xH_{2x}$)—S—($C_xH_{2x+1}$), or —($C_xH_{2x}$)—N($C_xH_{2x+1}$)$_2$;

$Ar^2$ is

[chemical structures showing various heterocyclic groups with $X$, $R^3$, $m$, and $N$ substituents]

wherein each $R^3$ is independently selected from hydrogen, $-(C_xH_{2x+1})$, $-(C_yH_{2y})-S-(C_xH_{2x+1})$, or $-(C_yH_{2y})-N(C_xH_{2x+1})_2$; X is sulfur, oxygen, selenium, or $N-R^4$, and $R^4$ is $-(C_xH_{2x+1})$; m is in integer of 1 to 4; x is an integer of 1 to 20; and y is an integer of 0 to 20.

One embodiment of the disclosure provides an optoelectronic conversion device, comprising the described dye.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein.

DETAILED DESCRIPTION

The following description is of the best-contemplated mode of carrying out the disclosure. This description is made for the purpose of illustrating the general principles of the disclosure and should not be taken in a limiting sense. The scope of the disclosure is best determined by reference to the appended claims.

One embodiment of the disclosure provides a dye having a chemical formula as shown in Formula 1:

(Formula 1)

[chemical structure of Formula 1 showing $Ar^1$, $Ar^2$, carbazole with $R^1$ substituents, and squaraine core]

In Formula 1, each $R^1$ is independently selected from hydrogen, $-(C_xH_{2x+1})$, $-(C_yH_{2y})-S-(C_xH_{2x+1})$, or $-(C_yH_{2y})-N(C_xH_{2x+1})_2$, wherein x is an integer of 1 to 20, and y is an integer of 0 to 20.

In Formula 1, $Ar^1$ is selected from one of Formulae 2 to 13.

(Formula 2)

[structure with HOOC, $R^2$, $N^+$]

(Formula 3)

[structure with HOOC, $R^2$, $N^+$, N]

(Formula 4)

[structure with HOOC, $R^2$, $N^+$]

(Formula 5)

[structure with HOOC, $R^2$, $N^+$, N]

(Formula 6)

[structure with HOOC, $R^2$, $N^+$, N]

(Formula 7)

[structure with HOOC, $R^2$, $N^+$]

(Formula 8)

[structure with HOOC, $R^2$, $N^+$, N]

(Formula 9)

[structure with HOOC, $R^2$, $N^+$]

(Formula 10)

(Formula 11)

(Formula 12)

(Formula 13)

In Formulae 2 to 13, each $R^2$ is independently selected from —$(C_xH_{2x+1})$, —$(C_xH_{2x})$—S—$(C_xH_{2x+1})$, or —$(C_xH_{2x})$—N$(C_xH_{2x+1})_2$, wherein x is an integer of 1 to 20.

In Formula 1, $Ar^2$ is selected from one of Formulae 14 to 21.

(Formula 14)

(Formula 15)

(Formula 16)

(Formula 17)

(Formula 18)

(Formula 19)

(Formula 20)

(Formula 21)

In Formulae 14 to 21, X is sulfur, oxygen, selenium, or N—$R^4$, and $R^4$ is —$(C_xH_{2x+1})$, wherein x is an integer of 1 to 20. In Formulae 14 to 21, each $R^3$ is independently selected from hydrogen, —$(C_xH_{2x+1})$, —$(C_yH_{2y})$—S—$(C_xH_{2x+1})$, or —$(C_yH_{2y})$—N$(C_xH_{2x+1})_2$, wherein x is an integer of 1 to 20, and y is an integer of 0 to 20. In Formulae 14 to 21, m is an integer of 1 to 4.

The dye can be, but is not limited to, be synthesized by the following steps.

As shown in Formula 22, $R^1$—Cl, carbazole, and $ZnCl_2$ (Lewis acid) are reacted via the Friedel-Crafts reaction. Furthermore, other positions of the carbazole can be firstly halogenated, and $R^1$ groups can be grafted on the other halogenated positions of the carbazole by a Heck reaction or the likes.

(Formula 22)

Subsequently, $Ar^2$—Br and the product in Formula 22 are reacted via a coupling reaction, as shown in Formula 23. In Formula 23, the catalyst of the coupling reaction can be Cu-bronze (e.g. Jourdan-Ullmann synthesis) or Pd (Buchwald-Hartwig coupling).

(Formula 23)

Squaric acid is chlorinated by SOCl$_2$, as shown in Formula 24.

(Formula 24)

The product in Formula 23, the product in Formula 24, and AlCl$_3$ (Lewis acid) are reacted via the Friedel-Crafts reaction, as shown in Formula 25.

(Formula 25)

Subsequently, the chloro group on the cyclobutene is substituted by a hydroxyl group, as shown in Formula 26.

(Formula 26)

Subsequently, a halide salt (e.g. iodide salt) of Ar$^1$—CH$_3$ and the product in Formula 26 are reacted to form a product (Formula 1), as shown in Formula 26.

(Formula 27)

Note that the method of synthesizing the dye in Formula 1 is not limited to Formulae 22 to 27, and those skilled in the art may synthesize the dye in Formula 1 by other methods if necessary.

In other embodiments of the disclosure, optoelectronic conversion devices including the described dye are disclosed. The optoelectronic conversion device can be planar display devices (e.g. organic light emitting diodes), organic photovoltaic devices, or solar cells (e.g. dye sensitized solar cells).

EXAMPLES

Example 1

Synthesis of Dye

Squaric acid (2.28 g, 40.0 mmole) was charged in a reaction bottle (100 mL). The reaction bottle was then purged by argon and vacuumed for several cycles to remove moisture therein. Benzene (17.5 mL) was then injected into the reaction bottle, and 8 drops of anhydrous DMF was then injected into the reaction bottle. Thionyl chloride (3.6 mL, 40 mmole) was then slowly injected into the reaction bottle to react with the squaric acid, and the reaction was heated to 90° C. to reflux for 12 hours. The resulting mixture was cooled to room temperature, and a major part of organic solvents thereof was removed by a rotary evaporator to obtain a condensed mixture. The condensed mixture was extracted by hexane, and then purified by re-crystallization and sublimation to obtain a yellow needle-shaped solid (0.8 g, yield=18%). The above reaction is shown in Formula 24, and the spectrum data of the product in Formula 24 is shown as follows. $^{13}$C-NMR (CDCl$_3$, 300 MHz, δ$_C$/ppm): 188.1 (2C, s); 189.41 (2C, s).

(Formula 24)

ZnCl$_2$ (62.5 g, 458.5 mmole) was charged in a reaction bottle (1000 mL), heated to 80° C., and vacuumed at 80° C. for 12 hours to remove moisture therein. Carbazole (25 g, 149.5 mmole) was charged in the reaction bottle, and then purged by argon and vacuumed for several cycles. Nitromethane (400 mL) and 2-chloro-2-methylpropane (49 mL) were sequentially added into the reaction bottle to serve as a solvent, and the reaction was stirred at room temperature for 7 days. Thereafter, de-ionized water (400 mL) was added into the resulting mixture to stir for tens of minutes. The mixture was extracted by dichloromethane, and the extraction (organic layer) was sequentially washed by a sodium carbonate solution, water, and brine. Anhydrous magnesium sulfate was added to the washed extraction to remove water thereof, and then filtered out to obtain a filtrate. A major part of organic solvents of the filtrate was removed by a rotary evaporator to obtain a condensed filtrate. The condensed filtrate was purified, by chromatography with a silica gel column (240-400 mesh) and a hexane/ethyl acetate (10/1) eluent, to obtain a white needle-shaped solid (15 g, yield=36%). The above reaction is shown in Formula 28, and the spectrum data of the product in Formula 28 is shown as follows. $^1$H-NMR (CDCl$_3$, 300 MHz, δ$_H$/ppm): 1.41 (18H, s), 7.30 (2H, d, 8.7 Hz), 7.44 (2H, d, 1.8 and 8.7 Hz), 8.05 (2H, d, 1.8 Hz).

(Formula 28)

The product in Formula 28 (9.33 g, 33.5 mmole), Cu-bronze (6.18 g, 33.5 mmole), and potassium carbonate (6.02 g, 43.6 mmole) were charged in a reaction bottle (500 mL). The reaction bottle was then purged by argon and vacuumed for several cycles to remove moisture therein. Nitrobenzene (150 mL) was injected into the reaction bottle to serve as a solvent, and 2-bromothiophene (3.9 mL, 40.2 mmole) was then injected into the reaction bottle. The reaction was heated to reflux for 7 days. Nitrobenzene of the refluxed mixture was removed by a rotary evaporator to obtain a condensed mixture. Ammonia was added to the condensed mixture to react for 2 hours. The resulting mixture was extracted by chloroform, and the extraction (organic layer) was sequentially washed by water and brine. Anhydrous magnesium sulfate was added to the washed extraction to remove water thereof, and then filtered out to obtain a filtrate. A major part of organic solvents of the filtrate was removed by a rotary evaporator to obtain a condensed filtrate. The condensed filtrate was purified, by chromatography with a silica gel column (200-400 mesh) and a hexane/ethyl acetate (10/1) eluent, to obtain a white solid (10.66 g, yield=88%). The above reaction is shown in Formula 29, and the spectrum data of the product in Formula 29 is shown as follows. $^1$H-NMR (CDCl$_3$, 300 MHz, δ$_H$/ppm): 1.45 (18H, s), 7.13 (2H, d), 7.32 (1H, dd, 2.7 and 4.2 Hz), 7.37 (2H, d, 8.7 Hz), 7.47 (2H, dd, 8.7 Hz), 8.09 (2H, d, 1.8 Hz).

(Formula 29)

AlCl$_3$ (1.03 g, 7.7 mole) and the product in Formula 29 (2.79 g, 7.7 mole) were charged in a reaction bottle (100 mL). The reaction bottle was then purged by argon and vacuumed for several cycles to remove moisture therein. The product in Formula 24 (2.58 g, 17.1 mmole) was dissolved in dichloromethane (25 mL) to be further injected into the reaction bottle, and the reaction was heated to reflux for 14 hours. The refluxed mixture was repeatedly extracted by chloroform, and the extraction (organic layer) was sequentially washed by a saturated brine and saturated ammonium chloride solution. Anhydrous magnesium sulfate was added to the washed extraction to remove water thereof, and then filtered out to obtain a filtrate. A major part of organic solvents of the filtrate was removed by a rotary evaporator to obtain a condensed filtrate. The condensed filtrate was purified, by chromatography with a silica gel column (200-400 mesh) and a dichloromethane/hexane (2/1) eluent, to obtain a yellow solid (0.66 g, yield=18%). The above reaction is shown in Formula 30, and the spectrum data of the product in Formula 30 is shown as follows. $^1$H-NMR (CDCl$_3$, 300 MHz, δ$_H$/ppm): 1.47 (18H, s), 7.47 (1H, d, 4.2 Hz), 7.56 (2H, dd, 1.8 and 8.7 Hz), 7.70 (2H, d, 8.7 Hz), 8.11 (2H, d, 1.8 Hz), 8.31 (1H, d, 4.2 Hz).

(Formula 30)

-continued

The product in Formula 30 (0.60 g, 1.3 mmole) was charged in a reaction bottle (100 mL), and THF (20 mL) was then injected into the reaction bottle under argon. Acetic acid (4.0 mL), water (4.0 mL), and 2N HCl (0.5 mL) were sequentially injected into the reaction bottle to reflux overnight. The refluxed mixture was cooled to room temperature and then vacuumed to remove solvents thereof. The vacuumed mixture was firstly purified by chromatography with a silica gel column (200-400 mesh) and a chloroform eluent to remove impurities thereof, and then purified by chromatography with the same silica gel column and a methanol eluent to obtain a yellow solid (0.14 g, yield=25.1%). The above reaction is shown in Formula 31, and the spectrum data of the product in Formula 31 is shown as follows. $^1$H-NMR (DMSO-d$^6$, 300 MHz, δ$_H$/ppm): 1.41 (18H, s), 7.36 (1H, d, 3.9 Hz), 7.46 (2H, d, 8.7 Hz), 7.53 (2H, dd, 1.8 and 8.7 Hz), 7.57 (1H, d, 3.9 Hz), 8.27 (2H, d, 1.8 Hz).

(Formula 31)

4-Hydrazinobenzoic acid (5 g, 33.0 mmole) was charged in a reaction bottle (250 mL), and ethanol (120 mL) was added into the reaction bottle to dissolve the 4-hydrazinobenzoic acid. 3-methyl-2-butanone (3.9 mL) and pure sulfuric acid (1 mL) were sequentially injected into the reaction bottle, and the reaction was heated to reflux for 12 hours. The refluxed mixture was repeatedly extracted by chloroform, and the extraction (organic layer) was then extracted by a saturated sodium bicarbonate solution. A pH value of the extraction (aqueous layer) was tuned to 4 by 1.2M HCl. The acidified extraction (aqueous layer) was then extracted by dichloromethane. Anhydrous magnesium sulfate was added to the extraction (dichloromethane layer) to remove water thereof, and then filtered out to obtain a filtrate. A major part of organic solvents of the filtrate was removed by a rotary evaporator, and another part of organic solvents of the filtrate was removed by vacuum. The vacuumed filtrate was purified, by re-crystallization in hexane, to obtain a red brown solid (4.24 g, yield=63.5%). The above reaction is shown in Formula 32, and the spectrum data of the product in Formula 32 is shown as follows. $^1$H-NMR (CDCl$_3$, 300 MHz, δ$_H$/ppm): 1.36 (6H, s), 2.36 (3H, s), 7.63 (1H, d, 8.1 Hz), 8.04 (1H, s), 8.14 (1H, dd, 1 and 8.1 Hz).

(Formula 32)

The product in Formula 32 (4.24 g, 20.9 mmole) was charged in a reaction bottle (100 mL). The reaction bottle was then purged by argon and vacuumed for several cycles to remove moisture therein. Acetonitrile (30 mL) was injected into the reaction bottle, and iodobutane (6.94 mL, 60.8 mmole) was then injected into the reaction bottle, and the reaction was heated to reflux for 20 hours under nitrogen. The refluxed mixture was cooled in ice bath and then filtered. The filtered cake was washed by acetonitrile to obtain a pink solid (7.10 g, yield=88%). The above reaction is shown in Formula 33, and the spectrum data of the product in Formula 33 is shown as follows. $^1$H-NMR (DMSO-d$^6$, 300 MHz, δ$_H$/ppm): 0.90 (3H, t, 7.2 Hz), 1.26-1.42 (6H, m), 1.55 (6H, s), 2.86 (3H, s), 4.45 (2H, t, 7.8 Hz), 8.07 (1H, d, 8.1 Hz), 8.16 (1H, d, 8.1 Hz), 8.37 (1H, s).

(Formula 33)

The product in Formula 31 (0.55 g, 1.2 mmole) was charged in a reaction bottle (100 mL), and a condenser system and a Dean-Stark apparatus were set on the reaction bottle. The product in Formula 33 (0.55 g, 1.4 mmole), butanol (30 mL), and benzene (30 mL) were sequentially added into the reaction bottle under argon, and the reaction was heated to reflux for 24 hours. The refluxed mixture was cooled to room temperature and then vacuumed to remove solvents thereof. The vacuumed mixture was purified, by chromatography with a silica gel column (240-400 mesh) and a chloroform/methanol (40/1) eluent, to obtain a blue solid (0.12 g, yield=14.4%). The above reaction is shown in Formula 34, and the spectrum data of the product in Formula 34 is shown as follows. $^1$H-NMR (DMSO-d$^6$, 300 MHz, δ$_H$/ppm): 0.95 (3H, t, 7.2 Hz), 1.25 (2H, m), 1.28-1.49 (4H, m), 1.43 (18H, s), 1.81 (6H, s), 4.46 (2H, t, 7.8 Hz), 6.63 (1H, s), 7.56 (3H, m), 7.63 (2H, d, 8.7 Hz), 7.85 (2H, m), 8.10 (1H, dd, 1.2 and 8.4 Hz), 8.27 (1H, s), 8.32 (2H, s). $^{13}$C-NMR (DMSO-d$^6$, 500 MHz, $\delta_C$/ppm); 13.61, 19.44, 24.85, 29.50, 31.68, 34.57, 45.00, 51.17, 65.61, 69.72, 92.48, 109.84, 113.48, 116.98, 123.59, 124.27, 124.33, 126.55, 128.29, 129.40, 130.26, 138.49, 143.26, 143.51, 144.20, 144.49, 161.82, 166.66, 177.01, 178.85, 180.17, 190.22. Elementary Anal. Calcd. for $C_{44}H_{46}N_2O_4S$: C: 75.61%; H: 6.63%; N: 4.01%; S: 4.59%. Found: C: 73.36%; H: 7.24%; N: 3.40%; S: 4.10%. FAB-MS (m/z): calcd for $C_{44}H_{46}N_2O_4S$ 698.91. found 699.28.

tered out to obtain a filtrate. A major part of organic solvents of the filtrate was removed by a rotary evaporator, thereby obtaining crude. The crude purity was checked by 1H-NMR, and the crude was directly used in a next synthesis step without purifying due to its high yield and high purity. The above reaction is shown in Formula 35, and the spectrum data of the product (crude) in Formula 35 is shown as follows. $^1$H NMR (CDCl$_3$, 300 MHz, $\delta_H$/ppm): 1.44 (18H, s), 7.14 (2H, m), 7.32 (1H, dd, 2.7 and 4.2 Hz), 7.37 (2H, d, 8.7 Hz), 7.47 (2H, dd, 8.7 Hz), 8.09 (2H, d, 1.8 Hz).

Example 2

Synthesis of Dye

The product in Formula 29 (9.18 g, 25.4 mmole) was charged in a reaction bottle (250 mL), and anhydrous THF (100 mL) was then added into the reaction bottle under argon. The reaction bottle was cooled to −78° C., n-butyl lithium (12.2 mL, 2.5M hexane solution) was injected into the reaction bottle, and the reaction bottled was warmed to room temperature. The reaction was performed at room temperature for 2 hours, and then cooled to −78° C. again. Trimethyl tin chloride (0.67 g, 30.5 mmole) was dissolved in anhydrous THF (100 mL) to be further injected into the reaction bottle at −78° C., and the reaction bottle was warmed to room temperature. The reaction was performed at room temperature for 13 hours. The resulting mixture was repeatedly extracted by chloroform, and the extraction (organic layer) was washed by a saturated brine. Anhydrous magnesium sulfate was added to the washed extraction to remove water thereof, and then fil- The product in Formula 35 (14.01 g, 26.7 mmole) was charged in a reaction bottle (250 mL). The reaction bottle was then purged by argon and vacuumed for several cycles to remove moisture therein. Anhydrous DMF (150 mL) was injected into the reaction bottle, and 2-bromothiophene (3.9 mL) was then injected into the reaction bottle. The reaction bottle was cooled to −78° C. to solidify the solution therein and then vacuumed. The reaction bottle was warmed to room temperature, and then purged by argon and vacuumed for several cycles. The steps of cooling to −78° C., vacuuming, warming to room temperature, and purging argon and vacuuming for several cycles were repeated 3 times. Pd(PPh$_3$)$_4$ (1.85 g, 1.6 mmole) was dissolved in anhydrous THF (50 mL) to be further added into the reaction bottle. The reaction was heated to reflux for 3 days. The refluxed mixture was repeatedly extracted by dichloromethane, and the extraction (organic layer) was sequentially washed by a saturated brine, ammonium chloride solution, and water. Anhydrous magnesium sulfate was added to the washed extraction to remove water thereof, and then filtered out to obtain a filtrate. A major part of organic solvents of the filtrate was removed by a rotary evaporator. The condensed filtrate was purified, by chromatography with a silica gel column (200-400 mesh) and a hexane eluent, to obtain a white solid (6.09 g, yield=51%). The above reaction is shown in Formula 36, and the spectrum data of the product in Formula 36 is shown as follows. $^1$H-NMR (CDCl$_3$, 300 MHz, $\delta_H$/ppm): 1.54 (18H, s), 7.03 (1H, dd, 3.6 Hz), 7.05 (1H, d, 3.9 Hz), 7.19 (1H, d, 3.6 Hz), 7.20 (1H, d, 1.5 Hz), 7.24 (1H, d, 0.9 Hz), 7.42 (2H, d, 8.7 Hz), 7.49 (2H, d, 8.7 Hz), 8.08 (1H, s).

The product in Formula 36 (2.52 g, 5.7 mmole) was charged in a reaction bottle (100 mL). The reaction bottle was then purged by argon and vacuumed for several cycles to remove moisture therein. AlCl$_3$ (0.43 g, 3.2 mmole) was then charged in the reaction bottle, and dichloromethane (10 mL) was injected into the reaction bottle to dissolve reactants. The product in Formula 24 (1.63 g, 10.8 mmole) was dissolved in dichloromethane (25 mL) to be further injected into the reaction bottle. The reaction was heated to reflux for 17 hours. The refluxed mixture was repeatedly extracted by chloroform, and the extraction (organic layer) was sequentially washed by a saturated brine and saturated ammonium chloride solution. Anhydrous magnesium sulfate was added to the washed extraction to remove water thereof, and then filtered out to obtain a filtrate. A major part of organic solvents of the filtrate was removed by a rotary evaporator. The condensed filtrate was purified, by chromatography with a silica gel column (200-400 mesh) and a hexane eluent, to obtain an orange solid (0.44 g, yield=18%). The above reaction is shown in Formula 37, and the spectrum data of the product in Formula 37 is shown as follows. $^1$H-NMR (CDCl$_3$, 300 MHz, $\delta_H$/ppm): 1.54 (18H, s), 7.03 (1H, dd, 3.6 Hz), 7.05 (1H, d, 3.9 Hz), 7.19 (1H, d, 3.6 Hz), 7.20 (1H, d, 1.5 Hz), 7.24 (1H, d, 0.9 Hz), 7.42 (2H, d, 8.7 Hz), 7.49 (2H, d, 8.7 Hz), 8.08 (1H, s).

The product in Formula 37 (0.44 g, 1.3 mmole) was charged in a reaction bottle (100 mL). Anhydrous THF (30 mL) was then injected into the reaction bottle. The reaction bottle was then purged by argon and vacuumed for several cycles to remove moisture therein. Acetic acid (5.0 mL), water (5.0 mL), and 2N HCl (2 mL) were sequentially and slowly injected into the reaction bottle to reflux overnight. The refluxed mixture was cooled to room temperature. A major part of organic solvents of the cooled mixture was removed by a rotary evaporator, and another part of organic solvents of the cooled mixture was removed by vacuum. The vacuumed mixture was firstly purified by chromatography with a silica gel column (200-400 mesh) and a chloroform eluent to remove impurities thereof, and then purified by chromatography with the same silica gel column and a methanol eluent to obtain a orange solid (0.12 g, yield=28.2%). The above reaction is shown in Formula 38, and the spectrum data of the product in Formula 38 is shown as follows. $^1$H-NMR (CDCl$_3$, 300 MHz, $\delta_H$/ppm): 1.47 (18H, s), 7.18 (1H, d, 3.9 Hz), 7.41 (1H, d, 4.2 Hz), 7.48 (1H, d, 3.9 Hz), 7.51 (2H, d, 1.2 Hz), 8.10 (2H, s), 8.12 (1H, d, 4.2 Hz).

(Formula 38)

(Formula 39)

The product in Formula 38 (0.46 g, 0.9 mmole) was charged in a reaction bottle (100 mL). The reaction bottle was then purged by argon and vacuumed for several cycles to remove moisture therein. A condenser system and a Dean-Stark apparatus were set on the reaction bottle. The product in Formula 33 (0.40 g, 1.0 mmole), benzene (25 mL), and butanol (25 mL) were sequentially added into the reaction bottle under argon, and the reaction was heated to reflux for 24 hours. The refluxed mixture was cooled to room temperature and then vacuumed to remove solvents thereof. The vacuumed mixture was purified, by chromatography with a silica gel column (200-400 mesh) and a chloroform/methanol (50/1) eluent, to obtain a blue solid (0.03 g, yield=4.5%). The above reaction is shown in Formula 39, and the spectrum data of the product in Formula 39 is shown as follows. $^1$H-NMR (DMSO-d$^6$, 300 M Hz, $\delta_H$/ppm): 0.93 (3H, t, 7.4 Hz), 1.40 (18H, s), 1.06-1.22 (4H, m), 1.79 (6H, s), 4.44 (2H, t, 4.8 Hz), 6.32 (1H, s), 7.41 (1H, d, 3.9 Hz), 7.49-7.56 (4H, d, 9.6 Hz), 7.60 (1H, d, 3.9 Hz), 7.65 (1H, d, 3.6 Hz), 7.72 (1H, d, 3.9 Hz), 7.83 (1H, d, 8.4 Hz), 8.09 (1H, d, 12.3 Hz), 8.26 (1H, s), 8.30 (2H, s). $^{13}$C-NMR (DMSO-d$^6$, 500 MHz, $\delta_C$/ppm): 13.61, 19.43, 24.83, 29.51, 31.72, 34.54, 43.50, 51.14, 72.00, 93.12, 99.31, 109.59, 116.87, 123.70, 124.08, 124.67, 125.31, 126.01, 126.65, 127.72, 128.95, 129.81, 130.34, 130.81, 133.93, 139.00, 139.59, 141.73, 143.77, 144.29, 161.71, 166.67, 177.04, 178.69, 180.75, 190.13. FAB-MS (m/z): calcd 781.04. found 781.2597.

Comparative Example 1

Synthesis of Dye

AlCl$_3$ (0.4 g, 3.0 mmole) was charged in a reaction bottle (100 mL). The reaction bottle was then purged by argon and vacuumed for several cycles to remove moisture therein. The product in Formula 24 (0.45 g, 3.0 mmole) was dissolved in dichloromethane (30 mL) to be further injected into the reaction bottle. 2-methylthiophene (0.29 g, 3.0 mmole) was dissolved in dichloromethane (10 mL) to be further injected into the reaction bottle. The reaction was then heated to reflux for 14 hours. The refluxed mixture was repeatedly extracted by chloroform, and the extraction (organic layer) was sequentially washed by a saturated brine and ammonia. Anhydrous magnesium sulfate was added to the washed extraction to remove water thereof, and then filtered out to obtain a filtrate. A major part of organic solvents of the filtrate was removed by a rotary evaporator. The condensed filtrate was purified, by chromatography with a silica gel column (200-400 mesh) and a hexane eluent, to obtain a yellow solid (0.25 g, yield=39%). The above reaction is shown in Formula 40, and the spectrum data of the product in Formula 40 is shown as follows. $^1$H-NMR (CDCl$_3$, 300 MHz, $\delta_H$/ppm): 2.66 (3H, s), 7.05 (1H, d, 3.9 Hz), 8.03 (1H, d, 3.9 Hz).

(Formula 40)

The product in Formula 40 (0.40 g, 1.3 mmole) was charged in a reaction bottle (100 mL). Acetic acid (5.35 mL), water (6.0 mL), and 2N HCl (0.82 mL) were sequentially and slowly injected into the reaction bottle to reflux for 13 hours. The refluxed mixture was repeatedly extracted by chloroform, and the extraction (organic layer) was sequentially washed by a saturated brine and ammonia. Anhydrous magnesium sulfate was added to the washed extraction to remove water thereof, and then filtered out to obtain a filtrate. A major part of organic solvents of the filtrate was removed by a rotary evaporator. The condensed filtrate was purified, by chromatography with a silica gel column (200-400 mesh) and a methanol eluent, to obtain a yellow solid (1.12 g, yield=32%). The above reaction is shown in Formula 41, and the spectrum data of the product in Formula 41 is shown as follows. $^1$H-NMR (CDCl$_3$, 300 MHz, $\delta_H$/ppm): 2.49 (3H, s), 6.89 (1H, d), 7.38 (1H, d).

(Formula 41)

The product in Formula 41 (0.5 g, 2.6 mmole) was charged in a reaction bottle (100 mL). The reaction bottle was then purged by argon and vacuumed for several cycles to remove moisture therein. A condenser system and a Dean-Stark apparatus were set on the reaction bottle. The product in Formula 33 (1.09 g, 2.8 mmole), butanol (40 mL), and benzene (40 mL) were sequentially added into the reaction bottle under argon, and the reaction was heated to reflux for 24 hours. The refluxed mixture was cooled to room temperature to be purified, by chromatography with a silica gel column (240-400 mesh) and a dichloromethane/methanol eluent, to obtain a blue solid (0.32 g, yield=28.8%). The above reaction is shown in Formula 42, and the spectrum data of the product in Formula 42 is shown as follows. $^1$H-NMR (DMSO-d$^6$, 300 MHz, $\delta_H$/ppm): 0.93 (3H, t, 7.2 Hz), 1.22-1.44 (4H, s), 2.57 (3H, s), 4.40 (2H, t, 6.9 Hz), 6.27 (1H, s), 7.04 (1H, d, 3.6 Hz), 7.62 (1H, d, 3.3 Hz), 7.80 (1H, d, 8.4 Hz), 8.07 (1H, d, 8.4 Hz), 8.24 (1H, s). $^{13}$C-NMR (DMSO-d$^6$, 500 MHz, $\delta_C$/ppm): 13.53, 15.56, 19.36, 24.94, 29.31, 44.67, 50.86, 91.71, 113.09, 123.49, 128.20, 128.66, 129.06, 129.46, 130.14, 142.98, 144.48, 147.63, 164.33, 166.62, 176.74, 178.28, 179.97, 190.98.

(Formula 42)

Example 3

Optoelectronic Properties of Dyes

The dye in Comparative Example 1 (the product in Formula 42), the dye in Example 1 (the product in Formula 34), and the dye in Example 2 (the product in Formula 39) were dissolved in ethanol to form dye solutions, respectively. The UV-VIS absorption spectra of the dye solutions are shown in Table 1 and FIG. 1.

TABLE 1

| Dye | Wavelength of maximum absorption ($\lambda_{max}$, nm) | Absorption coefficient ($\epsilon$, $M^{-1} cm^{-1}$) | Full width at half maximum (FWHM) |
|---|---|---|---|
| Comparative Example 1 | 568 | 85,791 | 63.2 |
| Example 1 | 603 | 68,694 | 114.0 |
| Example 2 | 612 | 134,151 | 100.3 |

As shown in Table 2, oxidation potentials of the dye solutions were measured by cyclic voltammetry (CV), and lowest unoccupied molecular orbital potentials ($E_{LUMO}$) of the dye solutions were calculated by energy gaps of the dye solutions.

TABLE 2

| Dye | Oxidation potential ($E^0_{ox}$) | Energy gap (Eg, V) | Lowest unoccupied molecular orbital potentials ($E_{LUMO}$) |
|---|---|---|---|
| Comparative Example 1 | 0.67 | 2.14 | −1.47 |
| Example 1 | 1.17 | 1.92 | −0.75 |
| Example 2 | 0.93 | 1.93 | −1.00 |

Figure 1:
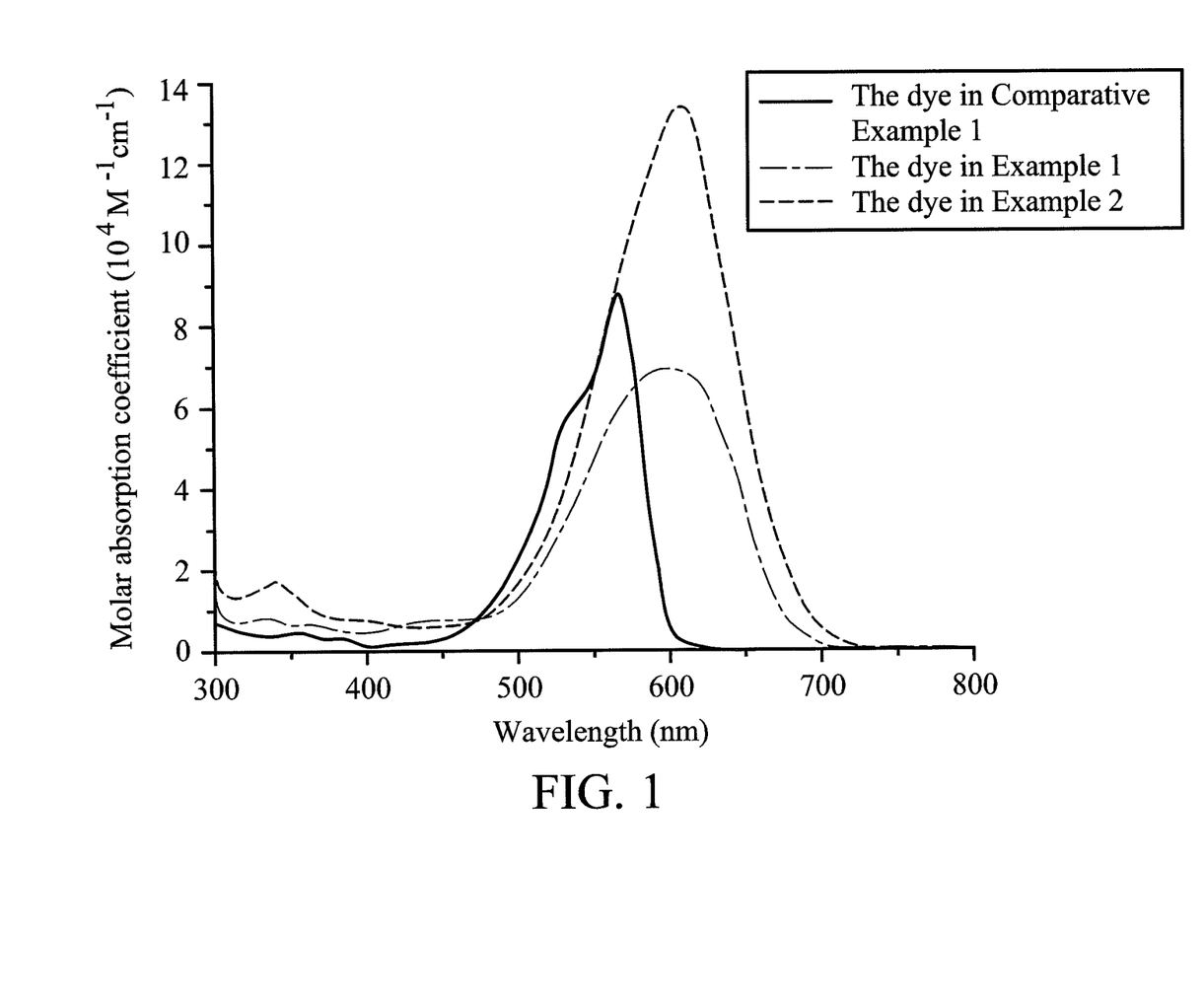
FIG. 1 shows UV-VIS absorption spectra of different dye solutions in one embodiment of the disclosure.

Accordingly to FIG. 1 and Table 2, the wavelength of maximum absorption of the dye was red-shifted by the carbazole group, and the full width at half maximum of the dye was increased by the carbazole group. As such, the dye having the carbazole group may have a wider absorption spectrum. The dye in Example 2 including most thiophene groups had the highest absorption coefficient (134.151 M$^{-1}$ cm$^{-1}$ at 612 nm). However, the optoelectronic conversion efficiency depends on not only the absorption coefficient of the dye, but also an oxidation-reduction potential difference between the dye and the TiO$_2$. When the oxidation-reduction potential of the dye is close to that of TiO$_2$, electrons will be easily transported to TiO$_2$. As shown in Table 2, the $E_{LUMO}$ of the dyes in Examples 1 and 2 are close to the $E_{LUMO}$ of TiO$_2$ (−0.5V). As such, the dyes in Examples 1 and 2 may more efficiently transport the electrons to TiO$_2$ than the dye in Comparative Example 1.

Example 4

Manufacturing Dye Sensitized Solar Cells

Figure 2:
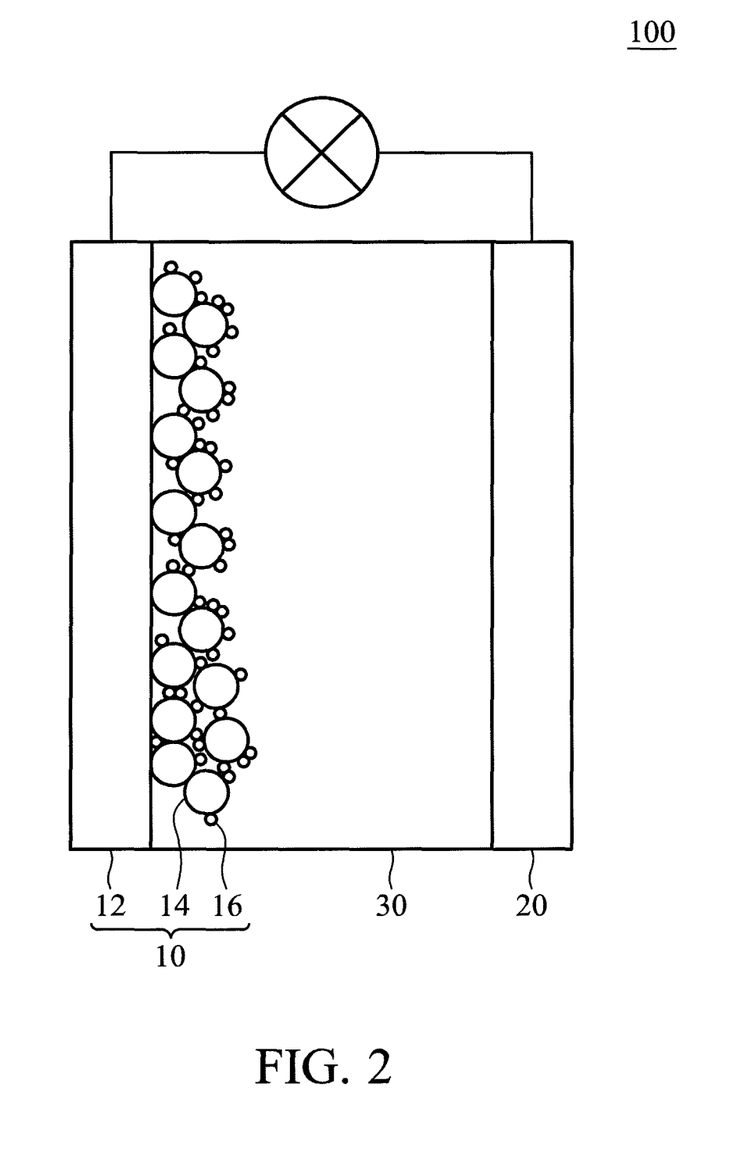
FIG. 2 shows a dye sensitized solar cell in one embodiment of the disclosure.

As shown in FIG. 2, the dye in Comparative Example 1 (the product in Formula 42), the dye in Example 1 (the product in Formula 34), and the dye in Example 2 (the product in Formula 39) were applied to manufacture dye sensitized solar cells 100, respectively. A working electrode 10, composed of a conductive substrate 12 and a porous titanium oxide layer 14 (18 μm) thereon, was dipped into an ethanol solution of dye 16 (2×10$^{-4}$M) for 5 hours, such that the dye 16 would be adsorbed on the titanium oxide layer 14 surface. The dye solution might further contain different concentrations of coadsorbents (Chenodeoxycholic acid, CDCA) to regularly arrange the dye with a lower stack degree. Next, the working electrode 10 was taken out of the dye solution, washed by a solvent, and dried. The dried working electrode 10 was assembled with an opposite electrode 20 and then sealed by a hot melt film or a UV glue. Subsequently, an electrolyte 30 (0.5M lithium iodide and 0.05M iodine dissolved in acetonitrile) was filled into a space between the working electrode 10 and the opposite electrode 20 through an injection hole. The injection hole was then sealed to complete the dye sensitized solar cell 100. Open circuit voltages (Voc), short-circuit current densities (Jsc), Fill factors (FF), and optoelectronic conversion efficiencies (η) of the dye sensitized solar cells including different dyes and different concentrations of coadsorbent CDCA are tabulated and shown in Tables 3 to 5.

TABLE 3

(The dye in Comparative Example 1, the product in Formula 42)

| CDCA concentration | Voc (V) | Jsc (mA/cm$^2$) | FF | η (%) |
|---|---|---|---|---|
| 0 mM | 0.306 | 2.72 | 0.57 | 0.48 |
| 10 mM | 0.349 | 3.19 | 0.63 | 0.71 |
| 20 mM | 0.339 | 2.78 | 0.61 | 0.58 |

TABLE 4

(The dye in Example 1, the product in Formula 34)

| CDCA concentration | Voc (V) | Jsc (mA/cm$^2$) | FF | η (%) |
|---|---|---|---|---|
| 0 mM | 0.315 | 4.53 | 0.63 | 0.96 |
| 10 mM | 0.415 | 5.15 | 0.66 | 1.41 |

TABLE 4-continued (The dye in Example 1, the product in Formula 34)

| CDCA concentration | Voc (V) | Jsc (mA/cm$^2$) | FF | η (%) |
|---|---|---|---|---|
| 20 mM | 0.400 | 6.39 | 0.65 | 1.66 |
| 30 mM | 0.426 | 6.99 | 0.64 | 1.91 |
| 40 mM | 0.419 | 7.29 | 0.64 | 1.96 |
| 50 mM | 0.427 | 8.63 | 0.63 | 2.31 |
| 60 mM | 0.473 | 8.00 | 0.68 | 2.59 |
| 70 mM | 0.469 | 6.82 | 0.65 | 2.07 |

TABLE 5

(The dye in Example 2, the product in Formula 39)

| CDCA concentration | Voc (V) | Jsc (mA/cm$^2$) | FF | η (%) |
|---|---|---|---|---|
| 0 mM | 0.315 | 4.38 | 0.63 | 0.87 |
| 10 mM | 0.338 | 4.41 | 0.63 | 0.94 |
| 20 mM | 0.391 | 5.84 | 0.64 | 1.46 |
| 30 mM | 0.410 | 5.77 | 0.67 | 1.60 |
| 40 mM | 0.416 | 7.41 | 0.66 | 2.03 |
| 50 mM | 0.411 | 8.17 | 0.66 | 2.22 |
| 60 mM | 0.431 | 7.16 | 0.66 | 2.05 |

The dye sensitized solar cells including the dyes in Comparative Example 1, Example 1, and Example 2 without the coadsorbent CDCA had optoelectronic conversion efficiencies (η) of 0.48%, 0.96%, and 0.87%, respectively. The optoelectronic conversion efficiencies of the dye sensitized solar cells including the dyes in Examples 1 to 2 were two times the optoelectronic conversion efficiency of the dye sensitized solar cell including the dye in Comparative Example 1. With the optimum CDCA concentration, the optoelectronic conversion efficiency of the dye sensitized solar cell including the dye in Comparative Example 1 (with 10 mM CDCA) was only improved to 0.71%, but the optoelectronic conversion efficiencies of the dye sensitized solar cells including the dye in Example 1 (with 60 mM CDCA) and the dye in Example 2 (with 50 mM CDCA) were largely improved to 2.59% and 2.22%, respectively. The optoelectronic conversion efficiencies of the dye sensitized solar cells including the dyes in Examples 1 to 2 with optimum CDCA concentration were three times the optoelectronic conversion efficiency of the dye sensitized solar cell including the dye in Comparative Example 1 with optimum CDCA concentration. As such, the dyes including a carbazole group in Examples 1 and 2 were better than the dye in Comparative Example 1 to manufacture a dye sensitized solar cell.

It will be apparent to those skilled in the art that various modifications and variations can be made to the disclosed methods and materials. It is intended that the specification and examples be considered as exemplary only, with a true scope of the disclosure being indicated by the following claims and their equivalents.

What is claimed is:

1. A dye, having a chemical formula:

wherein each $R^1$ is independently selected from hydrogen, $-(C_xH_{2x+1})$, $-(C_yH_{2y})-S-(C_xH_{2x+1})$, or $-(C_yH_{2y})-N(C_xH_{2x+1})_2$;

$Ar^1$ is wherein each $R^2$ is independently selected from $-(C_xH_{x+1})$, $-(C_xH_{2x})-S-(C_xH_{2x+1})$, or $-(C_xH_{2x})-N(C_xH_{2x+1})_2$;

$Ar^2$ is wherein each $R^3$ is independently selected from hydrogen, $-(C_xH_{2x+1})$, $-(C_yH_{2y})-S-(C_xH_{2x+1})$, or $-(C_yH_{2y})-N(C_xH_{2x+1})_2$;

X is sulfur, oxygen, selenium, or N—$R^4$, and $R^4$ is $-(C_xH_{2x+1})$;

m is in integer of 1 to 4;

x is an integer of 1 to 20; and y is an integer of 0 to 20.

2. The dye as claimed in claim 1, having a chemical formula:

3. The dye as claimed in claim 2, having a chemical formula:

4. The dye as claimed in claim 1, having a chemical formula:

5. The dye as claimed in claim 4, having a chemical formula:

6. An Optoelectronic conversion device, comprising the dye as claimed in claim 1.

7. An optoelectronic conversion device, comprising the dye as

7.
The optoelectronic conversion device as claimed in claim 6, being a planar display device.

8. The optoelectronic conversion device as claimed in claim 6, being an organic light emitting diode.

9. The optoelectronic conversion device as claimed in claim 6, being an organic photovoltaic device.

10. The optoelectronic conversion device as claimed in claim 6, being a solar cell.

11. The optoelectronic conversion device as claimed in claim 6, being a dye sensitized solar cell.

\* \* \* \* \*